(12) United States Patent
Wickham

(10) Patent No.: US 9,782,133 B2
(45) Date of Patent: *Oct. 10, 2017

(54) RESPIRATORY APPARATUS WITH IMPROVED FLOW-FLATTENING DETECTION

(71) Applicant: ResMed Limited, Bella Vista (AU)

(72) Inventor: Peter John Deacon Wickham, Five Dock (AU)

(73) Assignee: ResMed Limited (AU)

( * ) Notice: Subject to any disclaimer, the term of this patent is extended or adjusted under 35 U.S.C. 154(b) by 462 days.

This patent is subject to a terminal disclaimer.

(21) Appl. No.: 14/211,443

(22) Filed: Mar. 14, 2014

(65) Prior Publication Data

US 2014/0200476 A1   Jul. 17, 2014

Related U.S. Application Data

(63) Continuation of application No. 13/586,134, filed on Aug. 15, 2012, now Pat. No. 8,707,953, which is a
(Continued)

(51) Int. Cl.
*A61B 5/08* (2006.01)
*A61M 16/00* (2006.01)
(Continued)

(52) U.S. Cl.
CPC ............ *A61B 5/7278* (2013.01); *A61B 5/085* (2013.01); *A61B 5/087* (2013.01); *A61B 5/4818* (2013.01);
(Continued)

(58) Field of Classification Search
CPC ... A61B 5/0059; A61B 5/0068; A61B 5/0075; A61B 5/02055; A61B 5/05; A61B 5/055;
(Continued)

(56) References Cited

U.S. PATENT DOCUMENTS 4,777,962 A * 10/1988 Watson ................ A61B 5/7264
600/529
5,072,737 A   12/1991 Goulding
(Continued)

FOREIGN PATENT DOCUMENTS

DE        19706092 A1   8/1998
EP        0651971 A1    5/1995
(Continued)

OTHER PUBLICATIONS

International Preliminary Examining Authority, PCT Written Opinion for International Application No. PCT/AU01/01048, Mar. 7, 2002, pp. 1-8, Australia Patent Office, AU.
(Continued)

*Primary Examiner* — Annette Dixon
(74) *Attorney, Agent, or Firm* — Lerner, David, Littenberg, Krumholz & Mentlik, LLP

(57) ABSTRACT

In a respiratory apparatus for treatment of sleep apnea and other disorders associated with an obstruction of a patient's airway and which uses an airflow signal, an obstruction index is generated which detects the flattening of the inspiratory portion of the airflow. The obstruction index is used to differentiate normal and obstructed breathing. The obstruction index is based upon different weighting factors applied to sections of the airflow signal thereby improving sensitivity to various types of respiration obstructions.

8 Claims, 9 Drawing Sheets

Related U.S. Application Data continuation of application No. 11/611,315, filed on Dec. 15, 2006, now Pat. No. 8,739,789, which is a continuation of application No. 11/325,169, filed on Jan. 4, 2006, now Pat. No. 7,159,588, which is a continuation of application No. 10/950,926, filed on Sep. 27, 2004, now Pat. No. 7,013,893, which is a continuation of application No. 09/924,325, filed on Aug. 8, 2001, now Pat. No. 6,814,073.

(60) Provisional application No. 60/228,630, filed on Aug. 29, 2000.

(51) Int. Cl.
*A61B 5/00* (2006.01)
*A61B 5/085* (2006.01)
*A61B 5/087* (2006.01)
*A61M 16/06* (2006.01)

(52) U.S. Cl.
CPC ............ *A61B 5/7282* (2013.01); *A61M 16/00* (2013.01); *A61M 16/0069* (2014.02); *A61M 16/0066* (2013.01); *A61M 16/06* (2013.01); *A61M 2016/0039* (2013.01)

(58) Field of Classification Search
CPC ......... A61B 5/083; A61B 5/085; A61B 5/087; A61B 5/097; A61B 5/1102; A61B 5/1113; A61B 5/1114; A61B 5/1118; A61B 5/113; A61B 5/165; A61B 5/4041; A61B 5/4815; A61B 5/4818; A61B 5/6822; A61B 5/7203; A61B 5/7207; A61B 5/7221; A61B 5/7225; A61B 5/7228; A61B 5/7239; A61B 5/7257; A61B 5/726; A61B 5/7264; A61B 5/7267; A61B 7/003; A61M 16/00; A61M 16/0009; A61M 16/0051; A61M 16/0066; A61M 16/0069; A61M 16/0072; A61M 16/0075; A61M 16/06; A61M 16/16; A61M 16/204; A61M 16/205; A61M 2016/0021; A61M 2016/0027; A61M 2016/0036; A61M 2016/0039; A61M 2016/0069; A61M 2202/0208; A61M 2205/15; A61M 2205/3561; A61M 2230/04; A61M 2230/10; A61M 2230/14; A61M 2230/202; A61M 2230/205; A61M 2230/60; G01N 33/497; G06F 19/322; G06F 19/3406; G06F 19/345; G06K 9/00
USPC ............ 128/200.24, 201.23, 203.24, 204.18, 128/204.21, 204.22, 204.23, 204.26, 128/205.11, 205.12, 205.23, 912; 600/529, 531, 532, 533, 538, 543, 586

See application file for complete search history.

(56) References Cited

U.S. PATENT DOCUMENTS

| | | | |
|---|---|---|---|
| 5,101,820 A | 4/1992 | Christopher | |
| 5,148,802 A | 9/1992 | Sanders et al. | |
| 5,245,995 A | 9/1993 | Sullivan et al. | |
| 5,279,288 A | 1/1994 | Christopher | |
| 5,335,654 A | 8/1994 | Rapoport | |
| 5,392,768 A | 2/1995 | Johansson et al. | |
| 5,394,866 A | 3/1995 | Ritson et al. | |
| 5,404,871 A | 4/1995 | Goodman et al. | |
| 5,456,264 A | 10/1995 | Series et al. | |
| 5,485,851 A | 1/1996 | Erickson | |
| 5,490,502 A * | 2/1996 | Rapoport ............. | A61B 5/0002 128/204.21 |
| 5,497,764 A | 3/1996 | Ritson et al. | |
| 5,520,166 A | 5/1996 | Ritson et al. | |
| 5,535,738 A | 7/1996 | Estes et al. | |
| 5,535,739 A | 7/1996 | Rapoport et al. | |
| 5,542,410 A | 8/1996 | Goodman et al. | |
| 5,546,933 A | 8/1996 | Rapoport et al. | |
| 5,549,106 A | 8/1996 | Gruenke et al. | |
| 5,551,419 A | 9/1996 | Froehlich et al. | |
| 5,608,647 A | 3/1997 | Rubsamen et al. | |
| 5,622,162 A | 4/1997 | Johansson et al. | |
| 5,645,053 A | 7/1997 | Remmers et al. | |
| 5,645,054 A | 7/1997 | Cotner et al. | |
| 5,704,345 A | 1/1998 | Berthon-Jones | |
| 5,740,795 A | 4/1998 | Brydon | |
| 5,743,252 A | 4/1998 | Rubsamen et al. | |
| 5,755,218 A | 5/1998 | Johansson et al. | |
| 5,800,361 A | 9/1998 | Rayburn | |
| 5,803,066 A | 9/1998 | Rapoport et al. | |
| 5,826,570 A | 10/1998 | Goodman et al. | |
| 5,921,942 A | 7/1999 | Remmers et al. | |
| 5,944,680 A | 8/1999 | Christopherson et al. | |
| 5,947,115 A | 9/1999 | Lordo et al. | |
| 5,954,050 A | 9/1999 | Christopher | |
| 6,029,665 A | 2/2000 | Berthon-Jones | |
| 6,131,571 A | 10/2000 | Lampotang et al. | |
| 6,138,675 A | 10/2000 | Berthon-Jones | |
| 6,213,119 B1 | 4/2001 | Brydon et al. | |
| 6,213,955 B1 | 4/2001 | Karakasoglu et al. | |
| 6,273,859 B1 | 8/2001 | Remmers et al. | |
| 6,286,508 B1 | 9/2001 | Remmers et al. | |
| 6,299,581 B1 | 10/2001 | Rapoport et al. | |
| 6,305,374 B1 | 10/2001 | Zdrojkowski et al. | |
| 6,345,619 B1 | 2/2002 | Finn | |
| 6,363,933 B1 | 4/2002 | Berthon-Jones | |
| 6,367,474 B1 | 4/2002 | Berthon-Jones et al. | |
| 6,371,114 B1 | 4/2002 | Schmidt et al. | |
| 6,398,739 B1 | 6/2002 | Sullivan et al. | |
| 6,427,689 B1 | 8/2002 | Estes et al. | |
| 6,435,182 B1 | 8/2002 | Lutchen et al. | |
| 6,457,472 B1 | 10/2002 | Schwartz et al. | |
| 6,484,719 B1 | 11/2002 | Berthon-Jones | |
| 6,488,634 B1 | 12/2002 | Rapoport et al. | |
| 6,532,957 B2 | 3/2003 | Berthon-Jones | |
| 6,575,163 B1 | 6/2003 | Berthon-Jones | |
| 6,581,599 B1 | 6/2003 | Stenzler | |
| 6,588,422 B1 | 7/2003 | Berthon-Jones et al. | |
| 6,651,658 B1 | 11/2003 | Hill et al. | |
| 6,666,830 B1 | 12/2003 | Lehrman et al. | |
| 6,675,797 B1 * | 1/2004 | Berthon-Jones ....... | A61B 5/087 128/204.18 |
| 6,814,073 B2 | 11/2004 | Wickham | |
| 6,938,619 B1 | 9/2005 | Hickle | |
| 7,013,893 B2 | 3/2006 | Wickham et al. | |
| 7,159,588 B2 | 1/2007 | Wickham | |
| 8,707,953 B2 * | 4/2014 | Wickham ............. | A61M 16/00 128/200.24 |
| 2002/0023644 A1 | 2/2002 | Berthon-Jones | |

FOREIGN PATENT DOCUMENTS

| | | |
|---|---|---|
| EP | 1004325 A2 | 5/2000 |
| JP | 08512218 | 12/1996 |
| JP | 2000504602 A | 4/2000 |
| WO | 97/28838 A1 | 8/1997 |
| WO | 9924099 A1 | 5/1999 |

OTHER PUBLICATIONS

Japanese Application No. 2002-522971, Notice of Reasons for Rejection, Nov. 15, 2010, Japanese Patent Office.

Schwartz, A.R., et al., "Effect of positive nasal pressure on upper airway pressure-flow relationships", J.Appl.Physiol., pp. 1626-1634, 1989.

Smith, P.L., et al., "Upper airway pressure-flow relationships in obstructive sleep apnea", J.Appl.Physiol., 64(2):789-95, 1988.

* cited by examiner

RESPIRATORY APPARATUS WITH IMPROVED FLOW-FLATTENING DETECTION

CROSS-REFERENCE TO RELATED APPLICATIONS

This application is a continuation of U.S. application Ser. No. 13/586,134, filed Aug. 15, 2012 (now U.S. Pat. No. 8,707,953) which is a continuation of U.S. application Ser. No. 11/611,315, filed on Dec. 15, 2006 (now U.S. Pat. No. 8,739,789) which is a continuation of U.S. application Ser. No. 11/325,169 filed Jan. 4, 2006 (now U.S. Patent No. 7,159,588), which is a continuation of U.S application Ser. No. 10/950,926 filed Sep. 27, 2004 (now U.S. Pat. No. 7,013,893), which is a continuation of U.S. application Ser. No. 09/924,325 filed Aug. 8, 2001 (now U.S. Pat. No. 6,814,073) which claims priority filing date from U.S. Provisional Application No. 60/228,630 filed Aug. 29, 2000, all of which are hereby incorporated herein by reference.

FIELD OF THE INVENTION

This invention relates to a method and apparatus for detecting obstruction of the airway of a patient. More specifically, the invention involves an improved method and apparatus for detecting obstruction, either partial or complete, based upon a flattened measure of an inspiratory portion of respiratory airflow. The method is useful in patient ventilators such as those used in the diagnosis and treatment of respiratory conditions including sleep apnea or hypopnea.

BACKGROUND OF THE INVENTION

The dangers of obstructed breathing during sleep are well known in relation to the Obstructive Sleep Apnea (OSA) syndrome. Apnea, hypopnea and heavy snoring are recognized as causes of sleep disruption and risk factors in certain types of heart disease.

The monitoring of upper airway pressure-flow relationships in obstructive sleep apnea has been described in Smith et al., 1988, J. Appl. Physiol. 64: 789-795. FIG. 1 of that article shows polygraphic sleep recordings at varying levels of increasing nasal pressure. It was noted that inspiratory volumetric flow plateaued in certain breaths suggesting the presence of airflow limitation. Pressure-flow curves were constructed by plotting midinspiratory airflow against either mask pressure or endoesophageal pressure. The pressure-flow plots of nasal pressure against mean midinspiratory flow were then fit by least-squares linear regression to calculate resistance upstream to the collapsible site.

The effect of positive nasal pressure on upper airway pressure-flow relationships has been described in Schwartz et al., 1989, J. Appl Physiol. 66: 1626-1634. FIG. 4 of the article shows that pressure-flow tracings plateau at a low pressure level. It was further shown when the pressure was increased, flow did not plateau.

The common method of treatment of these syndromes is to administer Continuous Positive Airway Pressure (CPAP). The procedure for administering CPAP treatment has been documented in both the technical and patent literature. Briefly stated, CPAP treatment acts as a pneumatic splint of the airway by the provision of a positive pressure, usually in the range 4-20 cm $H_2O$. The air is supplied by a motor driven blower whose output passes via an air delivery device to sealingly engage a patient's airway. A mask, tracheotomy tube, endotracheal tube, nasal pillows or other appropriate device may be used. An exhaust port is provided in a delivery tube proximate to the air delivery device. Other forms of CPAP, such as bi-level CPAP, and self-titrating CPAP, are described in U.S. Pat. Nos. 5,148,802 and 5,245,995 respectively.

With regard to the control of CPAP treatment, various techniques are known for sensing and detecting abnormal breathing patterns indicative of obstruction. For example, U.S. Pat. No. 5,245,995 describes how snoring and abnormal breathing patterns can be detected by inspiration and expiration pressure measurements while sleeping, thereby leading to early indication of preobstructive episodes or other forms of breathing disorder. Particularly, patterns of respiratory parameters are monitored, and CPAP pressure is raised on the detection of pre-defined patterns to provide increased airway pressure to ideally prevent the occurrence of the obstructive episodes and the other forms of breathing disorder.

Similarly, U.S. Pat. No. 5,335,654 (Rapoport) lists several indices said to be indications of flow limitation and/or partial obstruction patterns including: (1) The derivative of the flow signal equals zero; (2) The second derivative between peaks of the flow signal is zero for a prolonged interval; (3) The ratio of early inspirational flow to midinspirational flow is less than or equal to 1. The patent further lists events said to be indications of obstructions: (1) Reduced slope of the line connecting the peak inspiratory flow to the peak expiratory flow; (2) Steep upward or downward stroke (dV/dt) of the flow signal; and (3) Ratio of inspiratory flow to expiratory flow over 0.5.

U.S. Pat. No. 5,645,053 (Remmers) describes calculating a flatness index, wherein flatness is defined to be the relative deviation of the observed airflow from the mean airflow. In Remmers, individual values of airflow are obtained between 40% and 80% of the inspiratory period. The mean value is calculated and subtracted from individual values of inspiratory flow. The individual differences are squared and divided by the total number of observations minus one. The square root of this result is used to determine a relative variation. The relative variation is divided by the mean inspiratory airflow to give a relative deviation or a coefficient of variation for that breath.

In commonly owned U.S. Pat. No. 5,704,345, Berthon-Jones also discloses a method for detecting partial obstruction of a patient's airway. Generally, the method involves a determination of two alternative obstruction index values based upon the patient's monitored respiratory airflow. Either obstruction index may then be compared to a threshold value. Essentially, the index values may be characterized as shape factors that detect a flattening of an inspiratory portion of a patient's respiratory airflow. The first shape factor involves a ratio of the mean of a midportion of the inspiratory airflow of the breathing cycle and the mean of the inspiratory airflow. The formula for shape factor 1 is as follows:

$$\text{shapefactor\_1} = \frac{\frac{1}{33}\sum_{t=16}^{48} f_s(t)}{M}$$

where $f_s(t)$ is a sample of the patient's inspiratory airflow and M is the mean of inspiratory airflow given by the following:

$$M = \frac{1}{65}\sum_{t=1}^{65} f_s(t)$$

A second shape factor involves a ratio of the Root Mean Square deviation of a midportion of inspiratory airflow and the mean inspiratory airflow according to the formula:

$$\text{shapefactor\_2} = \frac{\sqrt{\frac{1}{33}\sum_{t=16}^{48}(f_s(t)-M)^2}}{M}$$

Berthon-Jones further discloses a scaling procedure applied to the inspiratory airflow samples such that the mean M of the samples $f_s(t)$ is unity (M=1). This scaling procedure simplifies both shape factor formulas. Additional adjustments to $f_s(t)$ including averaging and the elimination of samples from erratic breaths such as coughs, sighs, hiccups, etc., are also taught by Berthon-Jones. The foregoing U.S. patent is hereby incorporated by reference.

The present invention involves an improved method and apparatus for detecting some forms of obstruction based upon the flattening of the inspiratory airflow.

BRIEF SUMMARY OF THE INVENTION

An objective of the present invention is to provide an apparatus in which obstruction, either partial or complete, of the patient's airway is detected by analyzing respiratory airflow.

A further objective is to provide an apparatus in which a novel algorithm for detecting airway obstruction is implemented without using additional components or making substantial changes to the structure of existing respiratory apparatus.

Accordingly, a respiratory apparatus is provided in which the respiratory airflow of a patient is continuously monitored. The part of respiratory airflow associated with inspiration is identified and sampled. From these inspiration samples, several samples representing a midportion of inspiration are identified. One or more weighting parameters or weighting factors are associated with each midportion sample. These weights and midportion samples are then used to calculate an obstruction index. Finally, this obstruction index is compared to a threshold value which comparison is used to adjust or control ventilatory assistance.

In one embodiment, weighting factors are applied based on whether the inspiratory airflow samples are less than or greater than a threshold level, such as the mean airflow.

In another embodiment, different weighting factors are applied to samples based on their time positions in a breath. Samples taken prior to a certain event during inspiration, for example, samples preceding the half way point of inspiration, are assigned lower weighting factors than samples succeeding the event. An obstruction index is then calculated using these samples with their corresponding weighting factors.

In one aspect, the subject invention pertains to a respiratory apparatus which includes a gas source adapted to selectively provide pressurized breathable gas to a patient, a flow sensor to sense the respiratory airflow from the patient and to generate an airflow signal indicative of airflow, an obstruction detector coupled to said flow sensor which includes a weight assigning member arranged to assign several weight factors to portions of the flow signal and to generate an obstruction signal using the weighted portions, and a controller coupled to the flow sensor and arranged to control the operation of the gas source, receive the obstruction signal and alter the operation of the gas source in response to the obstruction signal.

Another aspect of the invention concerns an apparatus for monitoring and/or treating a patient having a sleep disorder, the apparatus including a flow sensor that senses patient respiration and generates a corresponding flow signal; and an obstruction detector coupled to the flow sensor and adapted to determine a weighted average signal, the weighted average signal being dependent on a weighted average of the flow signal in accordance with one of an amplitude and a time position of portions of the flow signal, the obstruction detector including a signal generator that generates a signal indicative of an airway obstruction based on the weighted average signal.

A further aspect of the invention concerns an apparatus for treating a patient having a sleep disorder, the apparatus comprising a mask, a gas source selectively supplying pressurized breathable air to the patient through the mask, a flow sensor that senses airflow and generates a flow signal indicative of respiration, an obstruction detector coupled to the flow sensor and adapted to determine a weighted average signal, the weighted average signal being dependent on a weighted average of the flow signal in accordance with one of an amplitude and a time position of portions of the flow signal, and a controller receiving the obstruction signal and generating in response a command for activating the gas source.

Another aspect of the invention concerns a method for detecting obstruction in the airways of a patient, including measuring an air flow of the patient, detecting a predetermined section of said air flow, assigning weights to portions of said predetermined section and determining an index value for said predetermined section based on said weights as a measure of the obstruction.

DETAILED DESCRIPTION

Apparatus and Methodology

Figure 1:
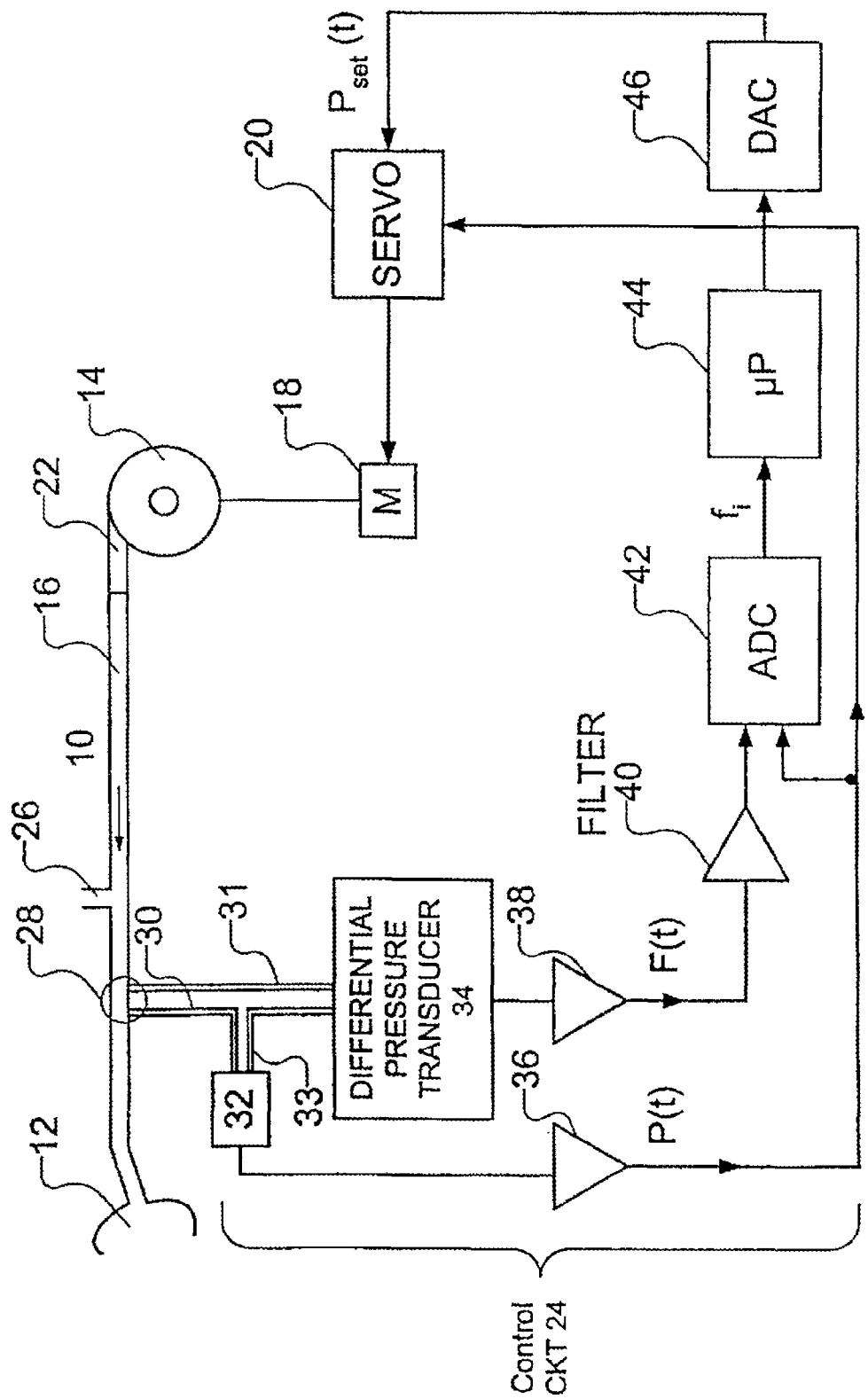
FIG. 1 shows a block diagram of a respiratory apparatus constructed in accordance with this invention.

FIG. 1 shows an example respiratory apparatus 10 constructed in accordance with the invention. The respiratory apparatus 10 includes a mask 12 connected to a blower 14 by a flexible tube 16. The mask 12 is fitted to the patient and may be either a nose mask or a face mask. The blower 14 with an air outlet 22 is driven by a motor 18 in accordance with control signals from a servocontroller 20. This arrangement allows the respiratory apparatus 10 to deliver pressurized air (or air enriched with oxygen from a source, not shown). The pressurized air is delivered by tube 16 to the mask 12. The tube 16 is provided with a narrow exhaust port 26 through which air exhaled by the patient is expelled.

A control circuit 24 is used to control the operation of servocontroller 20 and motor 18 using certain predetermined criteria, thereby defining modes of operation for the apparatus 10. Preferably, in accordance with this invention, the control circuit 24 is adapted to operate the apparatus 10 to provide CPAP to the patient.

Control circuit 24 includes a flow restrictive element 28. Tubes 30 and 31 lead from restrictive element 28 to a differential pressure transducer 34. Tube 30 is also connected through another tube 33 to a mask pressure transducer 32.

The mask pressure transducer 32 generates a first electrical signal which is amplified by an amplifier 36 to generate an output P(t) proportional to the air pressure within the mask 12. This output is fed directly to the servocontroller 20.

The differential pressure transducer 34 senses the differential pressure across the flow restrictive element 28, which differential pressure is related to the air flow rate through the flow restrictive element 28 and tube 16. Differential pressure transducer 34 generates a second electrical signal that is amplified by an amplifier 38. This amplified signal F(t) is termed an air flow signal since it represents the air flow through the tube 16.

The air flow signal F(t) is fed to a filter 40 which filters the signal within a preset range. The outputs of the filter 40 and amplifier 36 are fed to an ADC (analog-to-digital) converter 42, which generates corresponding signals $f_i$ to a microprocessor 44. The microprocessor 44 generates analog control signals that are converted into corresponding digital control signals by DAC 46 and used as a reference signal Pset (t) for the servo 20.

Figure 2:
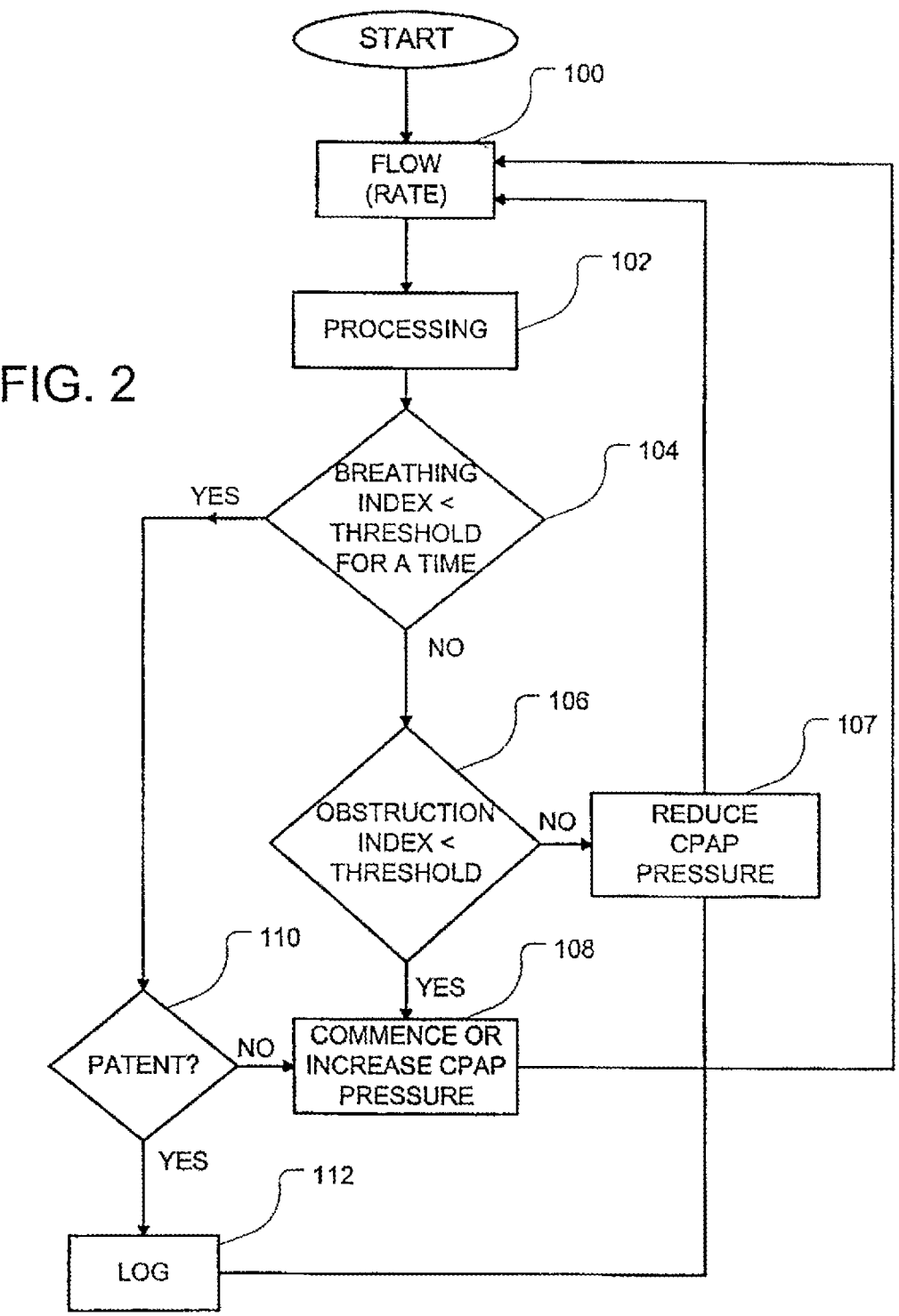
FIG. 2 shows a flow chart illustrating the operation of the apparatus of FIG. 1.

One method for the operation of a respiratory apparatus 10 is shown in the flow chart of FIG. 2. Individuals skilled in the art will recognize other methodologies for utilizing the improved flow flattening index that is disclosed herein. The embodiment of the methodology of FIG. 2 is also detailed in U.S. Pat. No. 5,704,345 (the '345 patent). The first step 100 is the measurement of respiratory flow (rate) over time. This information is processed in step 102 to generate Index values to be used as qualitative measures for subsequent processing. Thus, Step 102 includes the generation of obstruction index values based upon the weighting method as disclosed herein. Step 104 detects whether an apnea is occurring by comparison of the breathing Index with a threshold value.

If the answer in step 104 is "Yes", an apnea is in progress and there then follows a determination of patency in step 110. If there is patency of the airway, a central apnea with an open airway is occurring, and, if desired, the event is logged in step 112. If the result of step 110 is that the airway is not patent, then a total obstructive apnea or a central apnea with closed airway is occurring, which results in the commencement or increase in CPAP treatment pressure in step 108. If desired, step 108 may include the optional logging of the detected abnormality.

If the answer in step 104 is "No", one or more obstruction indices, such as the improved flow flattening indices, are compared with threshold values in step 106, by which the determination of obstruction of the airway is obtained. If the answer is "Yes" in step 106, then there is a partial obstruction, and if "No", there is no obstruction (normalcy).

Step 108 applies in the case of a complete or partial obstruction of the airway a consequential increase in CPAP treatment pressure. In the instance of normal breathing with no obstruction, the CPAP treatment pressure is reduced, in accordance with usual methodologies that seek to set the minimal pressure required to obviate, or at least reduce, the occurrence of apneas. The amount of reduction in step 107 may, if desired, be zero. Similarly, in the event of a central apnea with patent airway (step 110,112) treatment pressure is not increased. Such increases in pressure reflexively inhibit breathing, further aggravating the breathing disorder.

Improved Flow Flattening Indices

Figure 3:
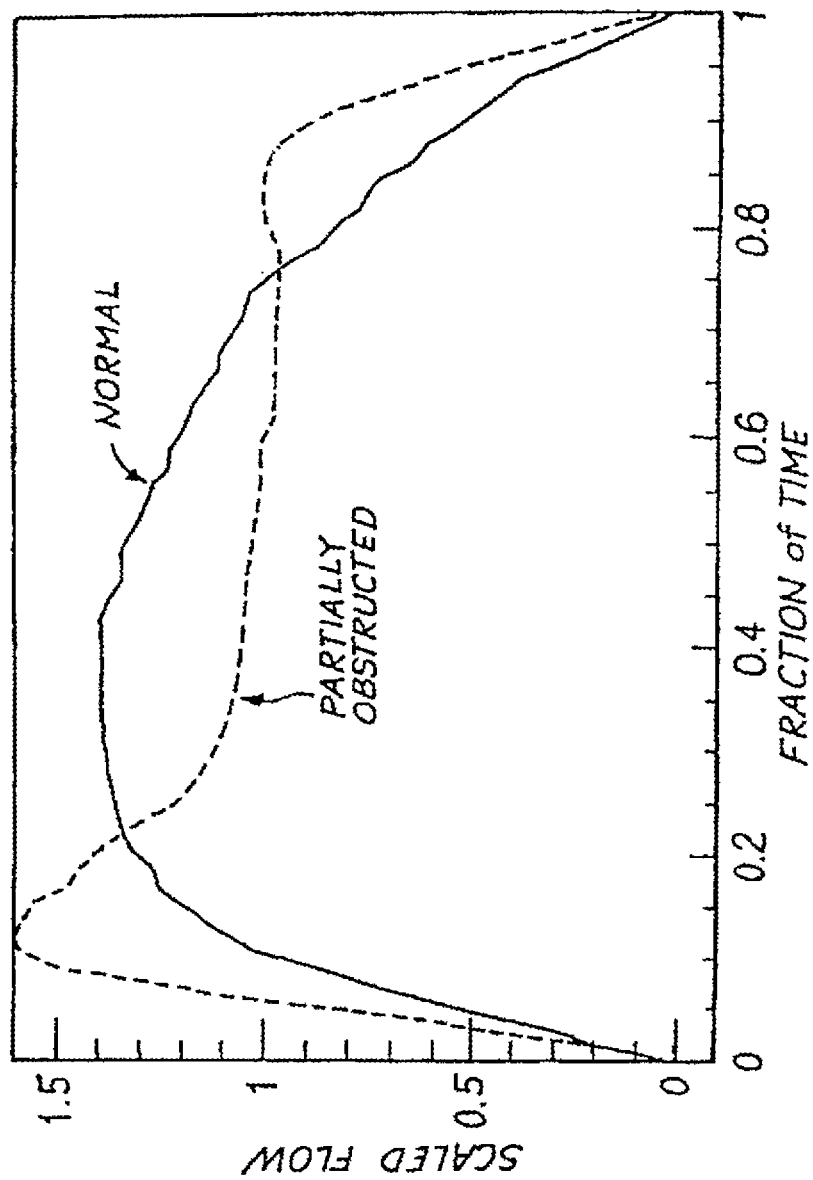
FIG. 3 shows the inspiration phases of typical respiration signals for a healthy person and a person with a partial airway obstruction.

FIG. 3 depicts an airflow signal with respect to the inspiratory portion of a typical breathing cycle. During the inspiratory portion of the breathing cycle of a healthy person, the airflow rises smoothly with inspiration, reaches a peak and falls smoothly to zero. However, a patient with a partially obstructed airway exhibits a breathing pattern characterized by a significant flat zone during inspiration. Theoretically, for an obstructed flow, as the degree of partial obstruction increases, the airflow signal for inspiration would tend to a square wave.

As previously discussed, the '345 patent describes two shape factors useful in testing for a flattening of the inspiratory portion of a patient's breathing cycle. In the preferred embodiment of the invention, the resulting obstruction index or flow flattening index (FFI) for each shape factor may be compared to unique threshold values. While the approach works well in many instances, it may not detect certain obstruction patterns.

Figure 4:
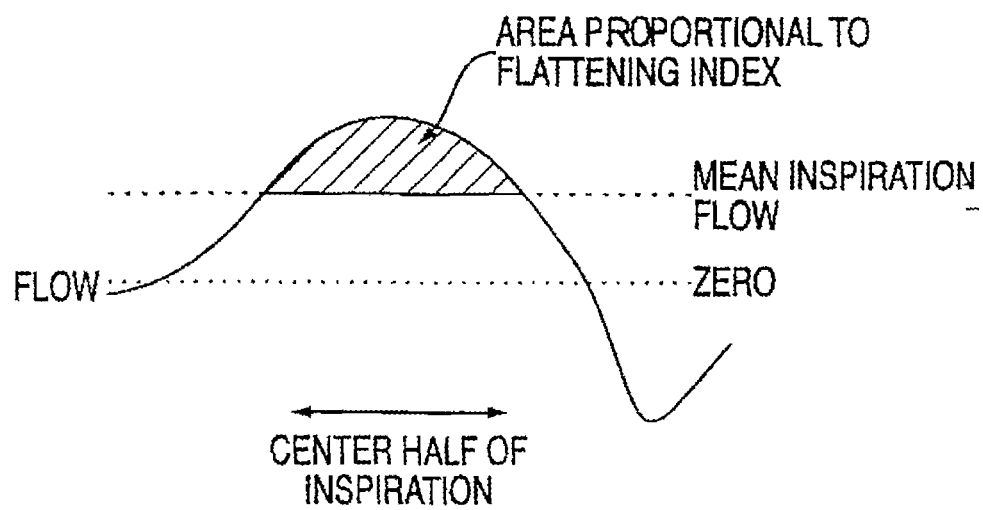
FIG. 4 shows a portion of a normal respiration signal from a patient.
Figure 5:
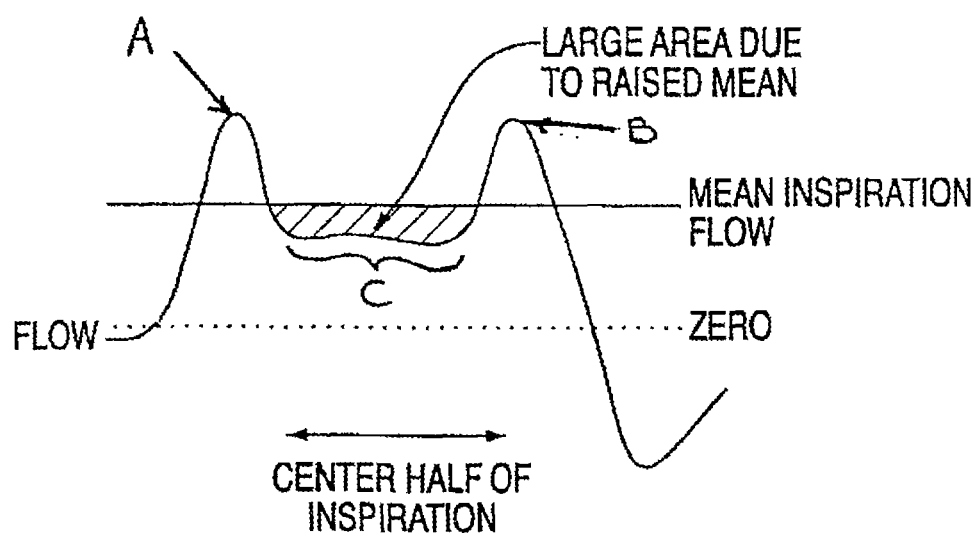
FIGS. 5 and 6 show portions of two different respiration signals characteristic from patients with sleep apnea.
Figure 6:
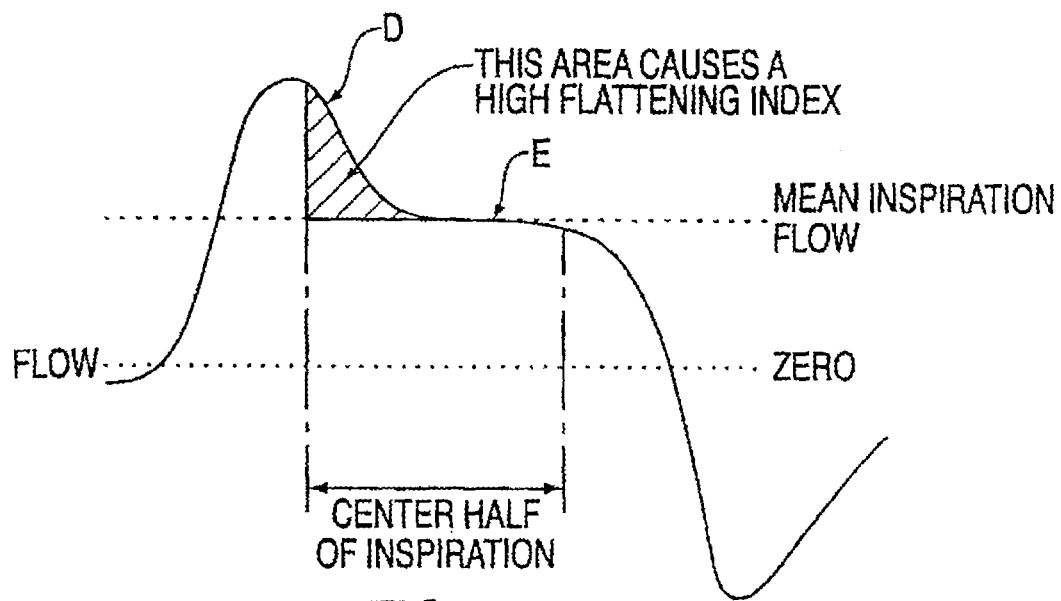

This can be illustrated by an examination of FIGS. 4-6. FIGS. 4-6 depict portions of respiration cycles. FIG. 4 shows a normal respiration flow and FIG. 5 shows a severely obstructed respiration cycle in which the inspiration period is characterized by two high positive lobes A and B and a relatively flat zone C between lobes A and B. In FIG. 4, the RMS deviation is indicated by the shaded area under the respiration flow curve and above the mean inspiration flow. In FIG. 5, the RMS deviation is indicated by the shaded area above the respiration flow curve and below the mean inspiration flow. As seen in FIG. 5, due to obstruction, the mean inspiration flow is greater than it would be without the second positive lobe B. Therefore, when analyzing the flow using shape factors of the '345 patent, the highly restricted and abnormal flow of FIG. 5 would not be detected as an obstruction.

Similarly, FIG. 6 shows another possible respiration curve for a patient with a partial airway obstruction. This curve includes an abnormally wide initial positive lobe D preceding a flat portion E. Once again, because of the large lobe D the mean inspiration flow is higher than for the more typical flow of FIG. 3. Using the prior art obstruction index, this condition may be detected as normal rather than being properly detected as an obstructed flow.

In order to detect these obstructions while continuing to properly respond to non-obstructed flows like the one of FIG. 4, the present invention assigns different weighting factors to the inspiration flow samples depending on:

(a) the magnitude of each sample with respect to the mean inspiration flow; and
(b) the time-wise position of each sample with respect to a time reference such as mid-inspiration.

By assigning a different weighting factor to a sample that is less than a particular value, for example, the mean flow, during the obstruction index or FFI calculation, there is an improved sensitivity to the respiration signal of FIG. 5 without affecting the FFI for normal breathing where most of the flow is greater than the mean.

Similarly, by assigning a different weighting factor to samples that occur after a time reference point, the subsequent samples become more significant. This improves sensitivity to the respiration signal of FIG. 6 without affecting the FFI for other breaths that are symmetrical in time about the center point of the inspiration.

Figure 7:
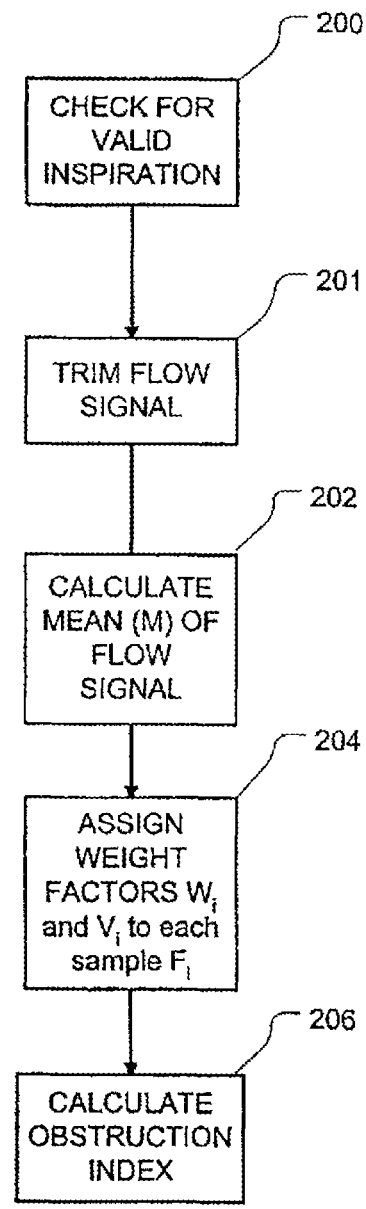
FIG. 7 shows a flow chart for determining the flattening indices for the respiration signals of FIGS. 4-6.

An algorithm using one form of the invention for calculating the improved FFI is shown in FIG. 7. In step 100 of FIG. 2, a typical flow rate curve F (defined by a plurality of samples $f_i$ where i is an index from 1 to the total number of samples n) is obtained. In step 200 of FIG. 7, the curve F is checked to insure that it is a valid inspiration curve. Next, in step 201 the curve F is trimmed to eliminate all samples $f_i$ outside of the inspiration period. Methods of implementing steps 200 and 201 are discussed in more detail below. In step 202, a mean M is calculated for all the inspiration samples 1 through n using conventional techniques.

In step 204 two weighting factors which may be designated as value dependent factors $w_i$ and time dependent factors $v_i$ are assigned to each of the samples $f_i$ based respectively on the amplitude of each sample and its time position in relation to the inspiration mean M and its center point respectively. For example, the factors $w_i$ and $v_i$ may be assigned for each flow measurement $f_i$ using the following rules:

A1. If $f_i > M$ then $w_i = 1$
A2. If $f_i < M$ then $w_i = 0.5$
B1. If $f_i$ is taken prior to the inspiration center point, then $v_i = 0.75$.
B2. If $f_i$ is taken after the inspiration center, then $v_i = 1.25$.

Next, in step 206 two alternative FFI or obstruction indices are calculated using the formulas:

$$\text{value\_weighted\_index} = \frac{\sum_{i=j}^{k} W_i \cdot |f_i M|}{M \cdot d}$$

$$\text{time\_weighted\_index} = \frac{\sum_{i=j}^{k} V_i |f_i - M|}{M \cdot d}$$

Where j is the first and k is the last sample relative to a midportion or center half of the inspiration curve F and d is the number of samples of the midportion of inspiration or center half as shown in FIGS. 3-6, and M is the mean of the inspiration curve F.

Alternatively, the algorithm may be described by the following steps:
Check the flow samples to confirm they represent a valid inspiration cycle with a shape within acceptable bounds.
Trim samples from any "pre-inspiratory period";
Find the mean of the inspiration flow samples;
Sum the weighed absolute difference of the flow samples from mean for samples in the center half or mid portion of inspiration:

If flow sample is > mean, sum the difference (flow-mean);
If flow sample is < mean, sum ½ the difference;
If flow sample is before the center point of the inspiration, use 75% of the difference from above;
If flow sample is after the center point of the inspiration, use 125% of the difference from above;
Scale the sum by the mean and inspiration time to produce the flattening index: FFI=weighed absolute sum/(Center half time*mean inspiration flow).

Figure 12:
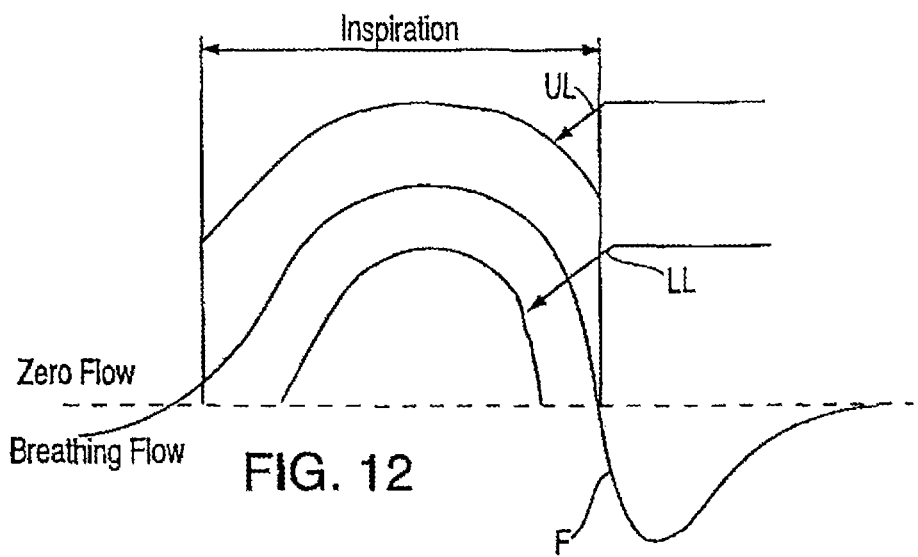
FIG. 12 shows an example of how a flow curve can be checked to insure that it is a valid respiration curve.

As discussed above, in step 200 of FIG. 7, the curve F is checked to insure that it corresponds to a valid inspiration curve. The flow curve F is checked against an upper and lower bound to prevent processing of an inspiratory curve corrupted by a cough, sigh, etc. For example, as shown in FIG. 12, the curve F may be rejected if it exceeds at any time an upper limit curve UL or falls below a lower limit curve LL. UL may be selected at about 150% of the mean inspiratory flow and LL may be selected at about 50% of the mean inspiratory flow.

In step 201 the respiration curve is trimmed to eliminate samples $f_i$ occurring before the actual inspiration period. One method of trimming includes the steps:
(1) determine the point where the flow reaches 75% of the peak inspiratory flow;
(2) determine the point where the flow reaches 25% of the peak inspiratory flow;
(3) extrapolate a line through these two points to the zero flow line to determine the point at the beginning of inspiration but use the first sample if the point is to the left of the first sample.

Figure 13:
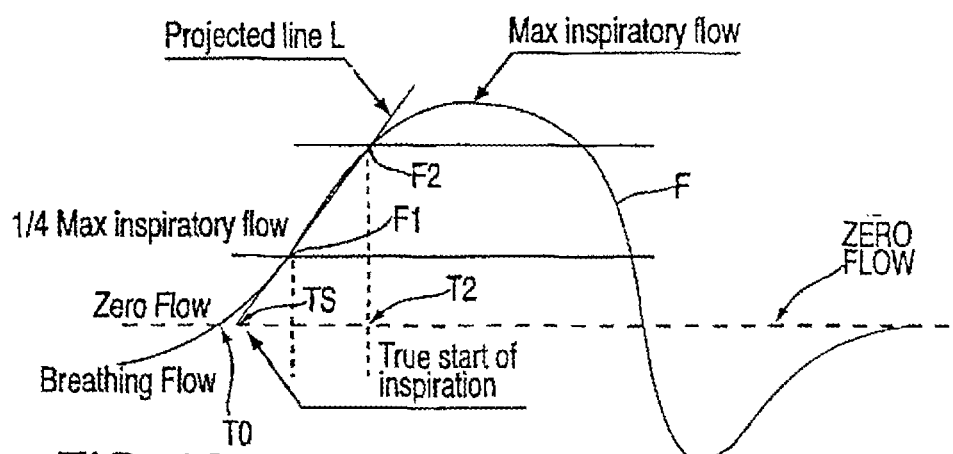
FIG. 13 shows an example of how a typical respiration flow curve can be trimmed.

This trimming method is illustrated in FIG. 13. With reference to the figure, the respiration curve F crosses the zero flow level at T0. Once the maximum inspiratory flow is reached, two intermediate flow levels are determined: the ¼ inspiratory flow level (i.e. the flow equaling 25% of the maximum inspiratory flow) and the ¾ inspiratory flow level (i.e. the flow equaling 75% of the maximum inspiratory flow). In FIG. 13, curve F crosses these two levels at points F1 and F2, respectively. Using the times T1 and T2, corresponding to the points F1 and F2, the curve F is approximated by a line L. This line is then extended to the zero flow level to determine an extrapolated time TS as the starting time for inspiration period for curve F. Samples $f_i$ obtained prior to TS are ignored.

The improvement resulting from the use of the above described value and time weighted obstruction indices can be seen with an examination of simulated tests. To this end, FIGS. 8, 9, 10 and 11 show breathing patterns of patients with both normal and obstructed respiration. These patterns were analyzed using the weighted indices of the present invention, as well as the shape factor 2 that uses equal weight samples $f_i$ as described in the '345 patent. The results of the tests are shown in the table below.

TABLE I

Figure 8:
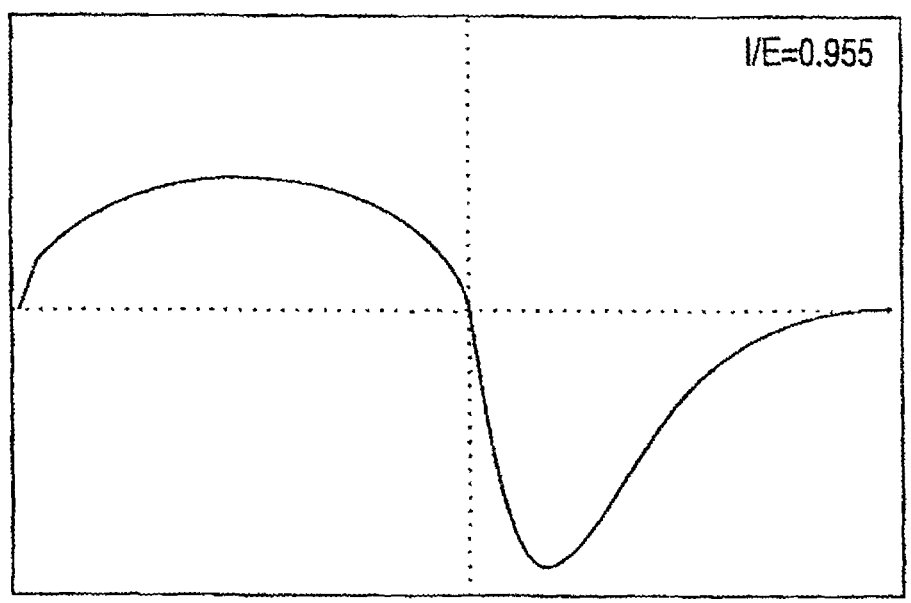
FIG. 8 shows a normal breathing pattern for a person without respiratory obstructions to illustrate the determination of two improved obstruction indices.
Figure 9:
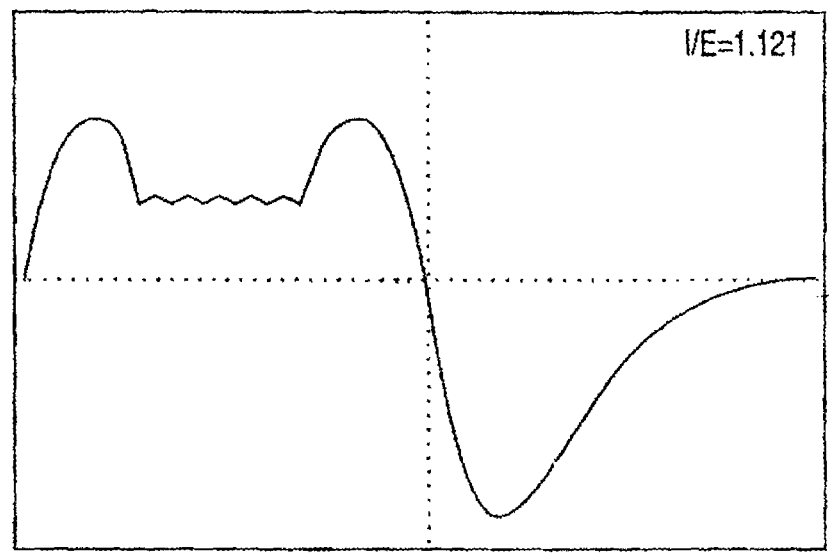
FIGS. 9, 10, and 11 show various breathing patterns with obstructions identifiable using the improved indices.
Figure 10:
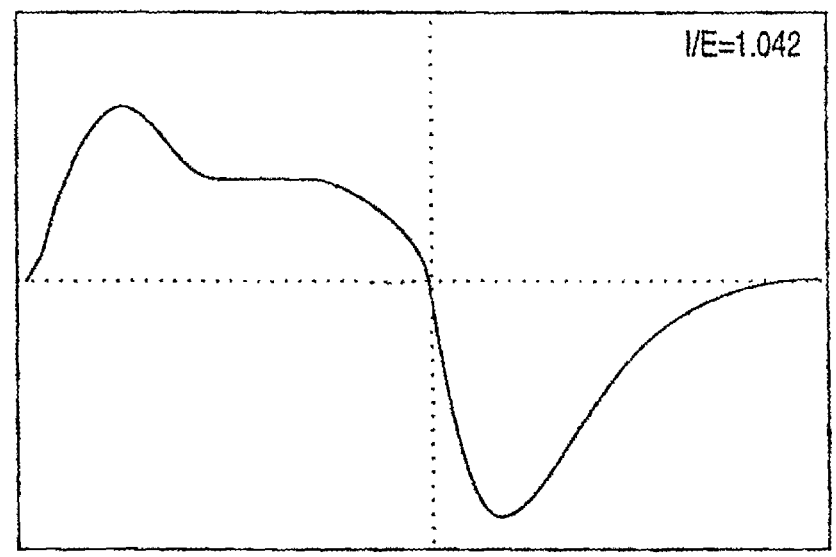
Figure 11:
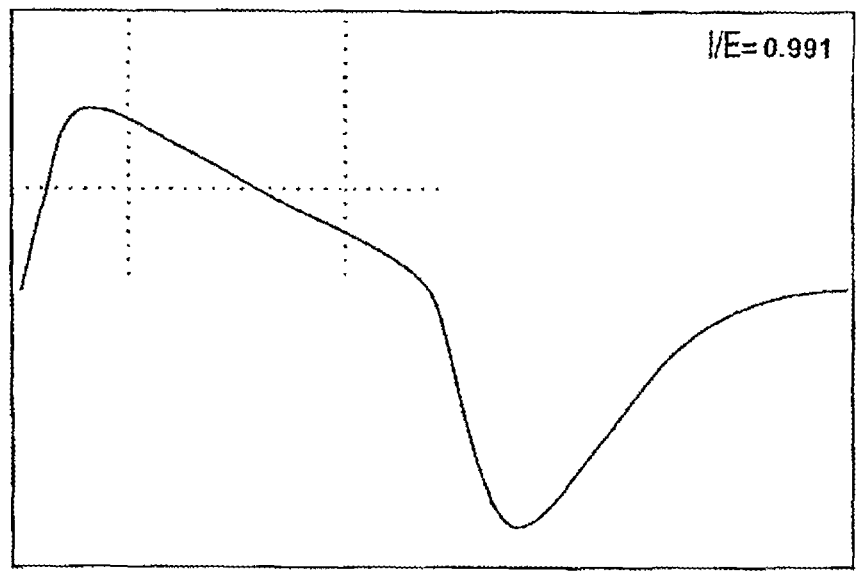

|  | Equal weight Index | Value weighted index | Time weighted index |
| --- | --- | --- | --- |
| FIG. 8 | 0.26 | 0.25 | 0.25 |
| FIG. 9 | 0.24 | 0.139 | 0.133 |
| FIG. 10 | 0.31 | 0.18 | 0.13 |
| FIG. 11 | 0.37 | 0.27 | 0.23 |

The weighted indices range from 0.3, which indicates no flattening or obstruction, to 0, which indicates gross obstruction. The separation point between these two classifications is 0.15, which may be used as a threshold value for comparison as described below.

FIG. 8 shows a normal breathing pattern. As can be seen from the table, all three indices have approximately the same value, thereby indicating that no increase in CPAP is needed.

FIG. 9 is similar in form to FIG. 5 in that it shows a pattern with two lobes separated by a relatively flat region. As seen in the table, if the equal weight index is used, no obstruction is found, while both improved indices are below the threshold and, therefore, both indicate an obstructed breathing pattern.

FIG. 10 shows a pattern similar to the one in FIG. 6 that starts off with a high initial lobe and then decays relatively slowly. For this pattern, the equal weight index and the value weighted index are both above the threshold. However, the time weighted index is below the threshold indicating an obstructed breathing pattern.

Finally, FIG. 11 shows another normal breathing pattern which has a shape somewhat different from the shape shown in FIG. 8. The three indices in the Table are all above the threshold level thereby indicating a normal pattern as well.

Although the invention has been described with reference to a particular embodiment, it is to be understood that this embodiment is merely illustrative of the application the principles of the invention. Thus, it is to be understood that numerous modifications may be made in the illustrative embodiment of the invention and other arrangements may be devised without departing from the spirit and scope of the invention. For example, while the preferred embodiment of the invention applies weighted samples to formulae which are used to identify a flattening of airflow, a similar method might be used with other formulae that detect roundness of flow or its deviation there from using a sinusoidal or other similar function.

The invention claimed is:

1. A method for determining the presence of a respiratory obstruction with a processor, the method comprising:
   accessing flow data samples from a signal generated by a sensor configured to detect flow, the flow data samples representing breath data; and
   generating an obstruction signal in an obstruction detector of the processor when at least one breathing cycle in the flow data samples has, during an inspiratory portion, two high positive lobes and a relatively flat zone between the lobes.

2. The method of claim 1, wherein at least some of the data samples are successive.

3. The method of claim 1, wherein at least some of the data samples are in regular intervals.

4. A method for determining a response for a respiratory obstruction with a processor, the method comprising:
   accessing data samples from a signal generated by a sensor configured to detect flow, the data samples representing breath data;
   detecting at least one breathing cycle in the data samples that has, during an inspiratory portion, two high positive lobes and a relatively flat zone between the lobes,
   calculating an obstruction index by assigning different weighting factors to inspiration flow samples depending on a magnitude of each sample with respect to a mean inspiration flow and a time-wise position of each sample with respect to a mid-inspiration point; and
   determining a command signal for activating or altering an operation of a respiratory apparatus, based on the calculated obstruction index.

5. An apparatus for determining the presence of a respiratory obstruction, the apparatus comprising:
   a processor configured to:
   access flow data samples from a signal generated by a sensor configured to detect flow, the flow data samples representing breath data; and
   generate an obstruction signal in an obstruction detector of the processor when at least one breathing cycle in the flow data samples has, during an inspiratory portion, two high positive lobes and a relatively flat zone between the lobes.

6. The apparatus of claim 5 wherein at least some of the data samples are successive.

7. The apparatus of claim 5 wherein at least some of the data samples are in regular intervals.

8. An apparatus for determining a response for a respiratory obstruction, the apparatus comprising:
   a processor configured to:
   access data samples from a signal generated by a sensor configured to detect flow, the data samples representing breath data;
   detect at least one breathing cycle in the data samples that has, during an inspiratory portion, two high positive lobes and a relatively flat zone between the lobes,
   calculate an obstruction index by assigning different weighting factors to inspiration flow samples depending on a magnitude of each sample with respect to a mean inspiration flow and a time-wise position of each sample with respect to a mid-inspiration point; and
   determine a command signal for activating or altering an operation of a respiratory apparatus, based on the calculated obstruction index.

* * * * *